United States Patent
Nath

(10) Patent No.: US 9,402,983 B1
(45) Date of Patent: Aug. 2, 2016

(54) VARIABLY EXPANDING BALLOON CATHETER

(71) Applicant: SaiNath Intellectual Properties, LLC, Largo, FL (US)

(72) Inventor: Iyunni Venkata Sesha Sayi Nath, Seminole, FL (US)

(73) Assignee: SaiNath Intellectual Properties, LLC, Largo, FL (US)

( * ) Notice: Subject to any disclaimer, the term of this patent is extended or adjusted under 35 U.S.C. 154(b) by 331 days.

(21) Appl. No.: 14/068,903

(22) Filed: Oct. 31, 2013

Related U.S. Application Data

(60) Provisional application No. 61/720,963, filed on Oct. 31, 2012.

(51) Int. Cl.
*A61M 29/00* (2006.01)
*A61M 29/02* (2006.01)
*A61M 25/10* (2013.01)

(52) U.S. Cl.
CPC ........... *A61M 29/02* (2013.01); *A61M 25/1002* (2013.01); *A61M 2025/1084* (2013.01)

(58) Field of Classification Search
CPC ..................... A61B 1/12022; A61B 17/12136; A61M 25/10; A61M 25/1002; A61M 2025/1081; A61M 2025/1084; A61M 25/1018; A61M 25/10184; A61M 25/104; A61M 29/00; A61M 29/02; A61M 2029/025; A61F 2/95; A61F 2/958
See application file for complete search history.

(56) References Cited

U.S. PATENT DOCUMENTS

| | | | | |
|---|---|---|---|---|
| 4,921,483 A * | 5/1990 | Wijay | ............... | A61M 25/1002 604/102.02 |
| 5,195,969 A * | 3/1993 | Wang | ................. | A61M 25/1029 604/103 |
| 5,409,495 A * | 4/1995 | Osborn | .................... | A61F 2/958 604/103.06 |
| 5,470,313 A * | 11/1995 | Crocker | ............ | A61M 25/1002 604/103.07 |
| 5,522,882 A * | 6/1996 | Gaterud | ..................... | A61F 2/07 606/192 |
| 5,645,560 A * | 7/1997 | Crocker | ............ | A61M 25/1002 606/108 |
| 5,755,690 A * | 5/1998 | Saab | ....................... | A61L 29/06 428/35.2 |
| 5,782,742 A * | 7/1998 | Crocker | ............... | A61N 5/1002 600/3 |
| 5,843,116 A * | 12/1998 | Crocker | ............ | A61M 25/1002 604/103.07 |
| 6,120,523 A * | 9/2000 | Crocker | ..................... | A61F 2/86 128/898 |
| 6,176,821 B1 * | 1/2001 | Crocker | ............... | A61N 5/1002 600/3 |

(Continued)

*Primary Examiner* — Jonathan W Miles
(74) *Attorney, Agent, or Firm* — Christopher Paradies; Paradies Law P.A.

(57) ABSTRACT

A variably expanding balloon catheter comprises a sequentially stepped outer shell when fully inflated, such as three sequentially increasing steps followed by three sequentially decreasing steps. For example, a balloon catheter comprises a sequentially stepped outer shell, when fully inflated, such that a first section of the outer shell is constrained to a first diameter by the sequentially stepped outer shell, and a second section, adjacent to the first section and attached to the first section by a step transition. The step transition provides a discontinuous change in diameter from the first diameter to the second diameter along a length of the balloon catheter, which may be abrupt.

13 Claims, 6 Drawing Sheets

(56) References Cited

U.S. PATENT DOCUMENTS

| | | | | |
|---|---|---|---|---|
| 6,258,019 B1* | 7/2001 | Verin | | A61M 25/10 600/1 |
| 6,409,741 B1* | 6/2002 | Crocker | | A61F 2/86 606/192 |
| 6,699,170 B1* | 3/2004 | Crocker | | A61N 5/1002 600/3 |
| 6,872,215 B2* | 3/2005 | Crocker | | A61F 2/86 606/192 |
| 7,189,229 B2* | 3/2007 | Lopath | | A61N 7/02 606/194 |
| 7,226,472 B2* | 6/2007 | Pederson, Jr. | | A61F 2/958 623/1.11 |
| 7,682,553 B2* | 3/2010 | Wang | | A61L 29/041 264/516 |
| 9,180,620 B2* | 11/2015 | Devens, Jr. | | A61M 25/1002 |
| 2001/0000350 A1* | 4/2001 | Durcan | | A61F 2/958 623/1.11 |
| 2002/0091435 A1* | 7/2002 | Campbell | | A61F 2/958 623/1.11 |
| 2003/0149466 A1* | 8/2003 | Gerberding | | A61F 2/958 623/1.11 |
| 2005/0043679 A1* | 2/2005 | Devens | | A61M 25/1002 604/103.06 |

\* cited by examiner

VARIABLY EXPANDING BALLOON CATHETER

CROSS RELATED APPLICATIONS

This application claims priority to U.S. Prov. Appl. 61/720,963, filed Oct. 31, 2012, which is hereby incorporated by reference in its entirety.

FIELD OF THE INVENTION

The field is balloon dilation and balloons used for balloon dilation.

BACKGROUND

Dilatation balloons are provided on the end of long catheters that can be introduced through body lumen, such as veins, arteries and other body lumens. For example, a deflated or partially inflated balloon may be positioned, such as by using optical imaging or radiological imaging, and then, the balloon is inflated to dilate the site of the lumen where it is positioned, using the force applied by hydrostatic pressure within the balloon. The balloon is deflated, and the catheter and the balloon are removed.

U.S. Pat. No. 5,163,989 is directed to a mold and method to form an inflatable member, such as a balloon for dilation catheters and the like which is free of parting lines. The mold in this reference has a continuous, unbroken inner mold surface defining a molding chamber with inner molding surface corresponding to the desired shape and dimensions for the working and tapered sections of a dilatation balloon. The mold body is made of glass or glass like material which is heat shrinkable in order to facilitate making the mold. To make shaped balloons, a tubular plastic member is placed within the inner mold chamber, inflated and heated. The plastic is pressed against the inner molding surface and is molded into the shape of the inner mold surface. The shaped balloon is cooled setting the size and shape of the balloon, and the balloon is deflated prior to removal of the balloon from the mold. The background of U.S. Pat. No. 5,163,989 disclosed uses for balloon catheters and methods used.

A mold of the type disclosed in U.S. Pat. No. 5,163,989 may be made using a variety of methods including machining, electrolytic erosion, die casting, or investment casting. Vacuum forming an inner mold surface, without parting lines, is disclosed in the detailed description of U.S. Pat. No. 5,163,989. Vacuum forming has the advantage that any shape of balloon may be made, without parting lines on the working or tapered surfaces of the balloon, which may have a smooth and continuous surface.

In order to implement vacuum forming, a heat-formable tubular member, which may be made of a glass or other material which may be softened at a glass-like softening transition temperature, is positioned around a core, which has a solid external surface shape of the desired balloon. The heat-formable tubular member is heated to a softening temperature. A vacuum is drawn internally or pressure is applied externally or both, and the tubular member collapses onto the surface of core. The tubular member is cooled below its oftening transition temperature. Then, the core is removed, such as by dissolution by a solvent. The tubular member is the inner surface of the mold and may be used to mold balloons using a parison disposed within the mold, a fluid such as nitrogen being introduced to expand a heated portion of a plastic tubular member that expands to take the shape of the inner surface of the mold.

SUMMARY

A variably expanding balloon catheter is formed to have a sequentially stepped outer shell when fully inflated. A dilatation balloon with a plurality of steps, such as three sequentially increasing steps followed by three sequentially decreasing steps may be formed. Such a balloon may be formed in a mold by inserting a plastic tubular member within a vacuum-formed mold and expanding a heated portion of the plastic tubular member to take the shape of the vacuum-formed mold.

A method of using a variable expanding balloon catheter uses a variably expanding dilatation balloon attached at an end of a catheter introduced through a body lumen. The variable expanding balloon catheter is positioned in the lumen, and the variably expanding dilatation balloon may be partially inflated, such as by monitoring the pressure introduced into the balloon. Then, the variably expanding dilatation balloon may be repositioned within the lumen at the point within the lumen where dilation is needed.

The sequentially-stepped surface of the variably expanding dilatation balloon allows the balloon to be expanding to one of a plurality of diameters, and a stepped shape provides for tactile feedback during position of the balloon with a lumen.

In one example, the plastic tubular member is designed with thickened regions along its length, such that a balloon formed during forming in a mold results in a balloon with walls having transitions from thicker to thinner wall thicknesses.

For example, variably expanding dilatation balloons may be made of a nondistendable polymer, such as a polyethylene teraphthelate. In one example, a balloon may be formed having a plurality of layers including an inner layer of polyethylene teraphthelate and an outer layer of a plastic elastomer. Multilayered balloons are disclosed in Wang et al., U.S. Pat. No. 5,195,969; U.S. application Ser. No. 08/130,283 and Hamilton et al., U.S. Pat. No. 6,129,737, the entire disclosure of which is hereby incorporated by reference herein. Examples of plastic elastomers may be made of styrenic block copolymers, polyolefin blends, elastomeric alloys, thermoplastic polyurethanes, thermoplastic copolyester and thermoplastic polyamides, for example.

In one example, a layer of a plastic elastomer, in a first thickness, is disposed on a first step of a sequentially-stepped, variable expanding dilatation balloon, a layer of a plastic elastomer, in a second thickness, is disposed on a second step of a sequentially stepped, variable expanding dilatation balloon, and a layer of a plastic elastomer, in a third thickness, is disposed on a third step of a sequentially-stepped, variable expanding dilatation balloon. For example, the first thickness may be less than the second thickness, which may be less than the third thickness.

In one example, a balloon catheter comprises a sequentially stepped outer shell, when fully inflated, such that a first section of the outer shell is constrained to a first diameter by the sequentially stepped outer shell, and a second section, adjacent to the first section and attached to the first section by a step transition, the step transition providing a discontinuous change in diameter from the first diameter to the second diameter along a length of the balloon catheter, and the second section is constrained to a second diameter by the sequentially stepped outer shell, the second diameter being greater than the first diameter. For example, the step transition may occur as a linearly increasing diameter from the first section to the second section along a length of the balloon catheter less than one-tenth of the length of either or both of the first section or second section. In one example, the step transition is abrupt, occurring along a length less than one-thirtieth of the length of the first section or second section.

BRIEF DESCRIPTION OF THE DRAWINGS

The following drawings are illustrative examples and do not further limit any claims that may eventually issue.

When the same reference characters are used, these labels refer to similar parts in the examples illustrated in the drawings.

DETAILED DESCRIPTION

Figure 1:
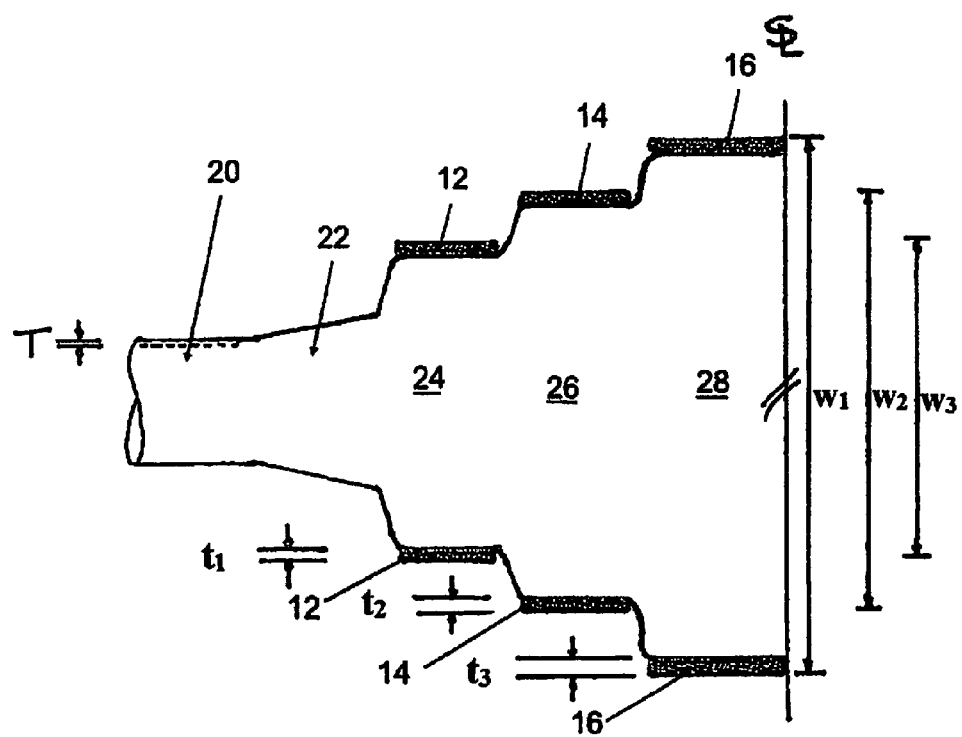
FIG. 1 illustrates one-half of an example of a fully-inflated, sequentially stepped, variable expanding dilatation balloon and a line of symmetry for an identical opposite half.

In FIG. 1, one-half of a fully-inflated, sequentially-stepped, variable expanding dilatation balloon is illustrated. A line of mirror symmetry (SL) is used to show a line of mirror symmetry, such that the opposite side of the balloon (not shown) is the same as the one illustrated in FIG. 1 only presenting a mirror image, such that the step-wise sequence is reversed and steps down to an end of the catheter 20. FIG. 1 illustrates a catheter 20 having a transition region 22 extending conically outward to a first step 24, a second step 26, and a third step 28, each progressively larger in diameter when the balloon 10 of the catheter 20 is fully inflated. FIG. 1 illustrates a series of bands 12, 14, 16, shown in cross-sectional view, which wrap around the circumference of each step 24, 26, 28. For example, the thickness or elastic modulus of each of the bands 12, 14, 16 may be varied to control the order in which each of the steps 24, 26, 28 expands, as illustrated in FIG. 2, for example.

Figure 2:
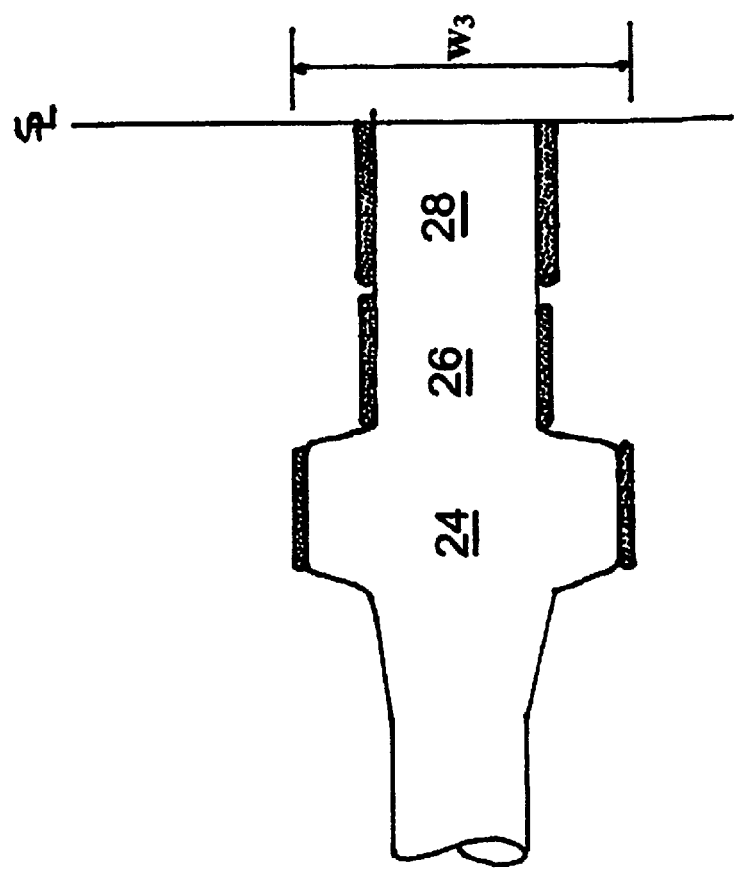
FIG. 2 illustrates a partially inflated view of the sequentially-stepped, variable expanding dilatation balloon of FIG. 1.

FIG. 2 illustrates an example wherein the first step 24 is surrounded by a first band 12 having a property which allows the first step 24 and the first band 12 to commence expanding prior to any substantial expansion of the second step 26 and the second band 14 or the third step 28 and the third band 16. For example, the first band 12 may have a modulus of elasticity that is less than the modulus of elasticity of both the second band 14 and the third band 16, or the first band 12 may have a first thickness ti that is less than the second thickness t2 of the second band 12 and the third thickness t3 of the third band 16, or the first band 12 may have a combination of thickness and modulus of elasticity of the first band 12, compared to the thicknesses and the moduli of the second band 14 and the third band 16, such that the first step 24 commences expanding at a pressure at which the other steps 26, 28 do not substantially expand. If the material or materials of the first step 24 form a comparatively inelastic step, such as a polymer that displays no or only a limited elasticity under hyrostatic pressure, and the diameter w3 of the first step is less than the diameters w2 and w1 of the second and third steps 26, 28, respectively, then increasing the hydrostatic pressure will lead to no further expansion of the first step 24 and will lead, eventually, to the expansion of the second step 26 and/or the third step 28, as the hydrostatic pressure continues to increase.

Figure 5:
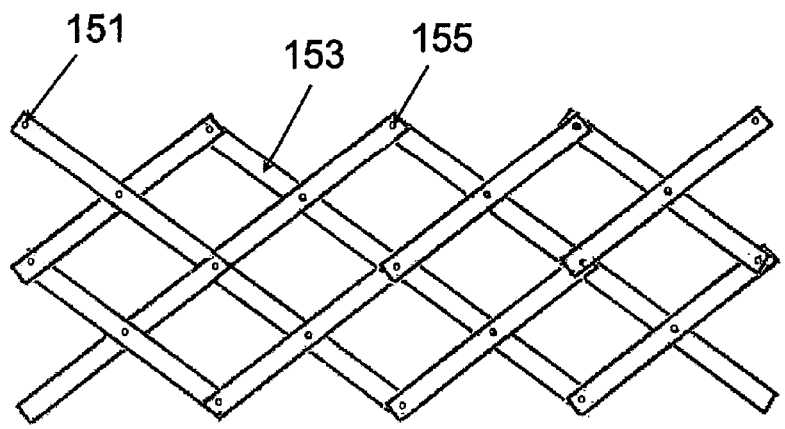
FIG. 5 illustrates one example of an extendable mesh used in the detail view of FIG. 4.

For example, a plastic material may be used to provide for expansion of each step 24, 26, 28 to a predetermined diameter W3, w2, wi, respectively. A plastic material may be made of a polyurethane film, which may be combined with a nondistendable mesh on or within layers of the polyurethane film, such as the example of a nondistendable mesh illustrated in FIG. 5. A nondistendable mesh may include a plurality of ligaments 153 coupled together one to the other by vertices 151, 155, and the mesh may be adhered to, incorporated in or sandwiched between a polymer film. In one example, the mesh may be made of nylon or aramid ligaments coupled together at vertices, e.g. mechanically fastened, fused, joined, knotted or welded, such that the mesh is capable of extending in one or more directions but being nondistendable in at least one direction. By nondistendable mesh, it is meant that the ligaments are not significantly elastic, having a comparatively high elastic modulus, such that elongation of the ligaments is minimal compared to the material in which the mesh is adhered, incorporated, embedded or sandwiched between. Thus, a mesh may unfold in one or more directions, but ligaments, themselves may be comparatively rigid, except for deflection, pivoting or rotation at the vertices, for example.

In another example, a variably expanding dilatation balloon may be made of a nondistendable polymer, such as a polyethylene teraphthelate. The polymer may unfold to expand to a particular diameter, but once the polymer is unfolded to its maximum diameter, the polymer is substantially inelastic and retains a comparatively fixed diameter, such that, if all of the polymer is unfolded, then the pressure within a balloon made of the polymer increases rapidly with the ingress of any additional gas or other fluid within the balloon at that point. Thus, a balloon made of a nondistendable polymer will show a characteristic increase in hydrostatic pressure when the balloon is unfolded to its nondistendable shape.

In one example, a balloon may be formed having a plurality of layers including an inner layer of polyethylene teraphthelate and an outer layer of a plastic elastomer. Multilayered balloons are disclosed in Wang et al., U.S. Pat. No. 5,195,969; U.S. application Ser. No. 08/130,283 and Hamilton et al., U.S. Pat. No. 6,129,737, the entire disclosure of which is hereby incorporated by reference herein. Examples of plastic elastomers may be made of styrenic block copolymers, polyolefin blends, elastomeric alloys, thermoplastic polyurethanes, thermoplastic copolyester and thermoplastic polyamides, for example. The drawing of FIG. 1 illustrates schematically, such a multilayered, stepped balloon having variable thickness (and/or elastic moduli) of each elastic layer (shown in cross sectional view for clarity) wrapped around a nondistendable, and for example a seamless, layer. In the example of FIG. 1, a seamless, nondistendable layer is formed as an inner layer upon which an elastic layer is formed or joined, for example.

Figure 6:
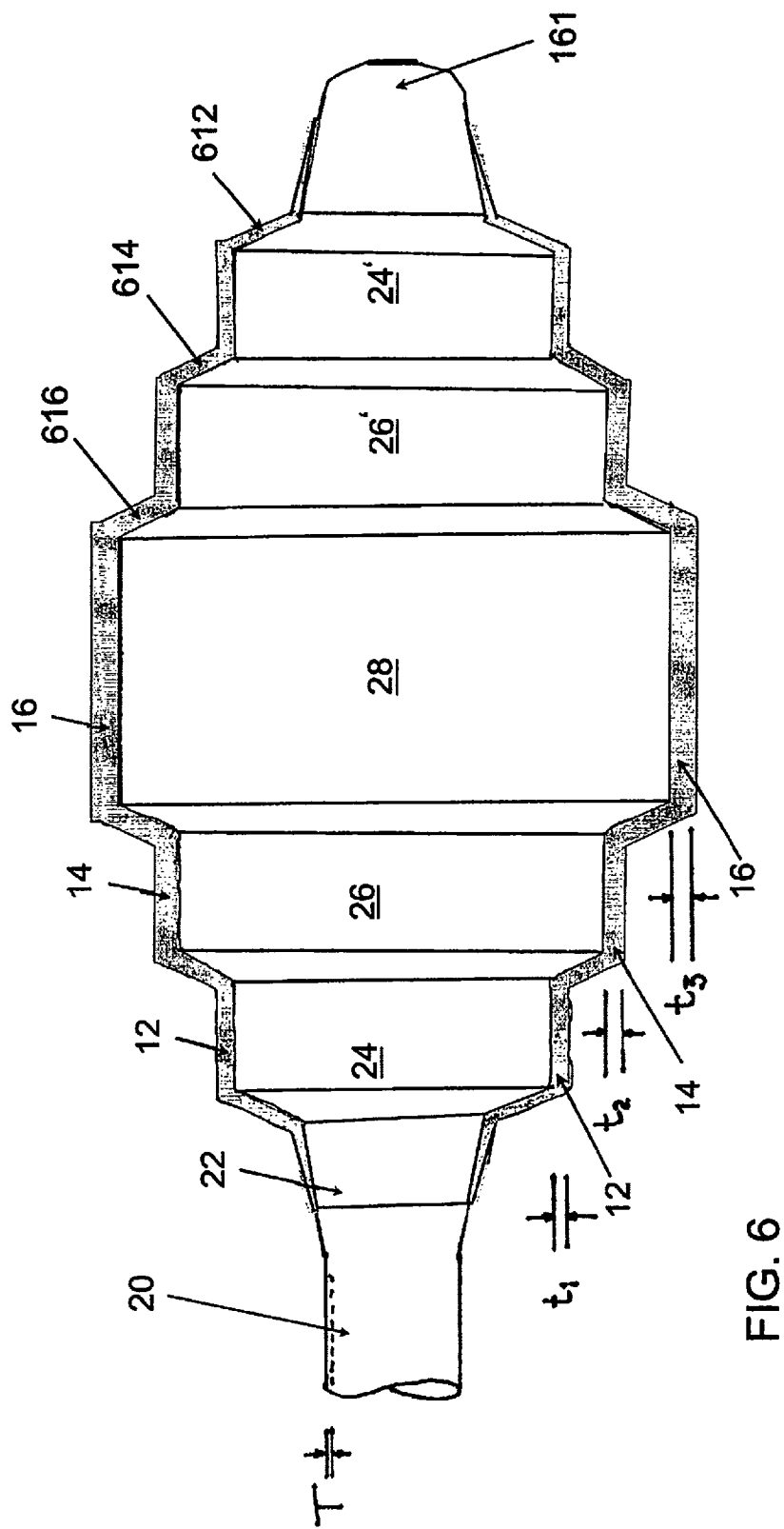
FIG. 6 illustrates a detail view of another example of a sequentially stepped, variable expandable balloon.

In an alternative example, the outer layer may be of a plastic elastomer nd may form a continuous outer layer with a plurality of thicknesses ti, t2, t3 and transition regions 612, 614, 616 between each of the plurality of thicknesses, as illustrated in the detail view of FIG. 6, for example, which shows both sides of a mirror symmetric balloon, with the outer layer in cross section (gray shaded) and an inner nondistendable film shown as a surface having conical regions and cylindrical regions, such regions having a substantially uniform film thickness, for example. For example, both layers may be seamless and may be formed by seamless processes. The inner layer may be formed as a film having a substantially constant film thickness, and the outer layer may be one or more layers formed or joined to the inner layer by deposition or otherwise. The outer layer may be formed of an elastomeric material or may comprise an elastomeric material and a mesh 624, as illustrated in FIG. 6, for example. The mesh may be applied, adhered, embedded or sandwiched between one or more layers of the elastomeric material in one or more regions of the balloon. The mesh may be included on one or more of the steps of the balloon, preventing the particular step from exceeding a particular diameter. For example, a fibrous mesh may comprise a band embedded in a conical or cylindrical region of the balloon to restrict expansion of the balloon in one or more directions when a particular diameter of a step is achieved by inflation with a hydrostatic pressure. By combining materials and mesh materials, a variety of shapes and sizes of stepped balloons with a plurality of stepped regions may be formed during inflation of a balloon, such as illustrated in FIG. 2, which shows a first region 24 inflated to a particular diameter w3 while the remaining regions 26, 28 are inflated less or not at all. FIG. 2 represents one-half of a mirror symmetric view of the balloon about the line SL.

Figure 3:
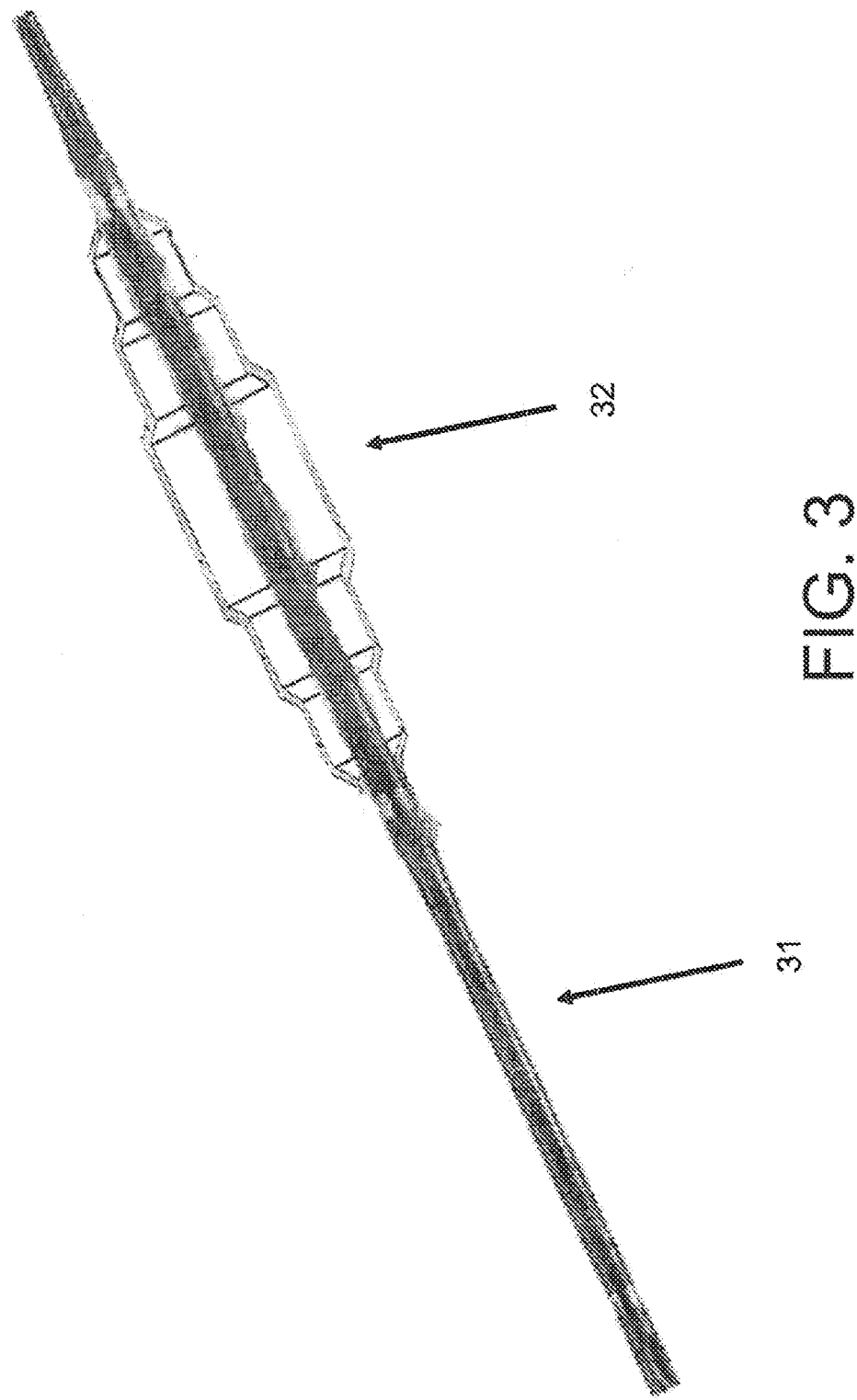
FIG. 3 illustrates a catheter including a variable expanding dilatation balloon, such as the sequentially-stepped, variable expanding dilatation balloon illustrated in FIGS. 1, 2, 4 and 6.

FIG. 3 illustrates a portion of a catheter 31 with a view of a variably expanding balloon 32 superimposed on the catheter, which is illustrated passing through the balloon in a partial cut-away view to expose the catheter as it traverses the balloon, the balloon being expanded as illustrated in the examples of FIGS. 1 and 6, for example.

Figure 4:
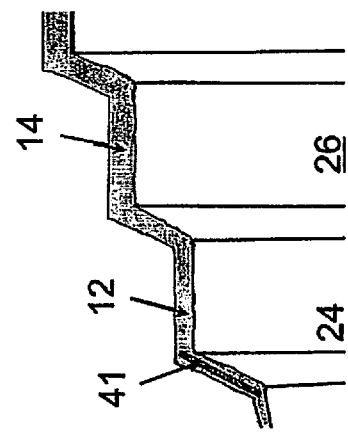
FIG. 4 illustrates a detail view of another example of a catheter with a sequentially-stepped, variable expanding balloon.

FIG. 4 illustrates a detail view of a mesh 41 embedded in a conically shaped section of a variably expanding balloon, which limits bulging of the conically-shaped section during inflation of the balloon with a fluid exerting pressure from within the balloon.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

What is claimed is:

1. A balloon catheter comprising a sequentially stepped outer shell, when fully inflated, such that:
   a first section of the outer shell is constrained to a first diameter, greater than an outer diameter of the catheter, when fully inflated, and
   a second section, adjacent to the first section and attached to the first section by a step transition,
   the step transition providing a discontinuous change in diameter from the first diameter to the second diameter along a length of the balloon catheter, and the second section is constrained to a second diameter, the second diameter being greater than the first diameter, wherein the sequentially stepped outer shell comprises at least three sequentially increasing steps, the step transition between the first section and the second section providing one of the three sequentially increasing steps, followed by at least three sequentially decreasing steps.

2. The balloon catheter of claim 1, wherein
   the first section has a first thickness and the second section has a second thickness, less than the first thickness; and
   the step transition has a thickness that transitions from the first thickness to the second thickness.

3. The balloon catheter of claim 1, wherein the sequentially stepped outer shell is comprised of a layer of a nondistendable polymer.

4. The balloon catheter of claim 3, wherein the sequentially stepped outer shell further comprises a layer of an elastomer.

5. The balloon catheter of claim 4, wherein the elastomer is a plastic elastomer.

6. The balloon catheter of claim 5, wherein the nondistendable polymer comprises a polyethylene teraphthelate.

7. The balloon catheter of claim 5, wherein the plastic elastomer comprises styrenic block copolymers, polyolefin blends, thermoplastic polyurethanes, thermoplastic copolyester or thermoplastic polyamides.

8. The balloon catheter of claim 7, wherein the plastic elastomer comprises styrenic block copolymers.

9. The balloon catheter of claim 1, further comprising a mesh embedded in the step transition.

10. The balloon catheter of claim 1, comprising a first band is disposed on an outer diameter of the first section, and a second band is disposed on an outer diameter of the second section.

11. The balloon catheter of claim 1, further comprising a mesh embedded in a thickness of the first section or the second section.

12. The balloon catheter of claim 1, further comprising a tube extending through the sequentially stepped outer shell and connected at opposite ends of the sequentially stepped outer shell.

13. A method of using the balloon catheter of claim 1, comprising:
   inserting the catheter of claim 1 into a lumen of a patient;
   positioning the catheter of claim 1 within the lumen;
   at least partially inflating the catheter of claim 1, such that at least one of the first section or the second section are dilated, completely;
   repositioning the catheter of claim 1 within the lumen; and
   continuing inflation of the catheter of claim 1, such that the second section is dilated, completely.

\* \* \* \* \*